(12) United States Patent
Korenevski et al.

(10) Patent No.: US 9,737,608 B2
(45) Date of Patent: Aug. 22, 2017

(54) PHYTOGLYCOGEN NANOPARTICLES AND METHODS OF MANUFACTURE THEREOF

(71) Applicant: Mirexus Biotechnologies Inc., Guelph (CA)

(72) Inventors: Anton Korenevski, Guelph (CA); Erzsebet Papp-Szabo, Guelph (CA); John Robert Dutcher, Guelph (CA); Oleg Stukalov, Kitchener (CA)

(73) Assignee: MIREXUS BIOTECHNOLOGIES INC., Guelph (CA)

( * ) Notice: Subject to any disclaimer, the term of this patent is extended or adjusted under 35 U.S.C. 154(b) by 0 days.

(21) Appl. No.: 14/787,207

(22) PCT Filed: Apr. 25, 2014

(86) PCT No.: PCT/CA2014/000380
§ 371 (c)(1),
(2) Date: Oct. 26, 2015

(87) PCT Pub. No.: WO2014/172786
PCT Pub. Date: Oct. 30, 2014

(65) Prior Publication Data
US 2016/0114045 A1    Apr. 28, 2016

Related U.S. Application Data

(60) Provisional application No. 61/816,686, filed on Apr. 26, 2013.

(51) Int. Cl.
| | |
|---|---|
| *A61K 47/36* | (2006.01) |
| *A61K 8/73* | (2006.01) |
| *C08L 5/00* | (2006.01) |
| *A61Q 17/04* | (2006.01) |
| *A61Q 19/00* | (2006.01) |
| *A61K 8/04* | (2006.01) |
| *C08B 37/00* | (2006.01) |
| *A61K 8/02* | (2006.01) |
| *A61K 9/16* | (2006.01) |
| *A23L 19/00* | (2016.01) |
| *A23L 33/10* | (2016.01) |
| *A61Q 5/06* | (2006.01) |
| *A61Q 15/00* | (2006.01) |
| *A61Q 17/00* | (2006.01) |
| *A61Q 19/10* | (2006.01) |

(52) U.S. Cl.
CPC ............ *A61K 47/36* (2013.01); *A23L 19/00* (2016.08); *A23L 33/10* (2016.08); *A61K 8/0241* (2013.01); *A61K 8/046* (2013.01); *A61K 8/73* (2013.01); *A61K 9/16* (2013.01); *A61Q 17/04* (2013.01); *A61Q 19/00* (2013.01); *C08B 37/0009* (2013.01); *C08L 5/00* (2013.01); *A23V 2002/00* (2013.01); *A61K 2800/10* (2013.01); *A61Q 5/06* (2013.01); *A61Q 15/00* (2013.01); *A61Q 17/005* (2013.01); *A61Q 19/002* (2013.01); *A61Q 19/10* (2013.01)

(58) Field of Classification Search
CPC . A61K 47/36; A61K 9/16; A61K 8/73; A61Q 5/06
USPC ............. 424/401; 428/402; 514/777; 435/97
See application file for complete search history.

(56) References Cited

U.S. PATENT DOCUMENTS

| | | | |
|---|---|---|---|
| 4,630,393 A | 12/1986 | Bonucci | |
| 5,597,913 A | 1/1997 | Nicoletti et al. | |
| 5,734,045 A | 3/1998 | Nicoletti et al. | |
| 5,895,686 A | 4/1999 | Horino et al. | |
| 6,146,857 A | 11/2000 | Pauly et al. | |
| 6,451,362 B1 | 9/2002 | Singh et al. | |
| 7,670,812 B2 | 3/2010 | Kajiura et al. | |
| 8,986,771 B2 * | 3/2015 | Yao | ............... 426/602 |
| 9,422,585 B2 | 8/2016 | Zhang | |
| 2010/0272639 A1 * | 10/2010 | Dutcher | ............. A61K 47/4823 424/1.37 |
| 2011/0269849 A1 | 11/2011 | Yao | |
| 2014/0066363 A1 | 3/2014 | Bhunia et al. | |
| 2014/0186495 A1 | 7/2014 | Yao | |
| 2014/0303365 A1 | 10/2014 | Zhang | |
| 2015/0080220 A1 | 3/2015 | Yao et al. | |

FOREIGN PATENT DOCUMENTS

| | | |
|---|---|---|
| EP | 0860448 B1 | 8/1998 |
| WO | 97/21828 A1 | 6/1997 |
| WO | 0044232 A1 | 8/2000 |
| WO | 2009081287 A2 | 7/2009 |

(Continued)

OTHER PUBLICATIONS

Author: M G James; title: Characterization of the maize gene sugary1, a determinant of starch composition in kernels, The Plant Cell; Apr. 1995, vol. 7 No. 4 417-429.*
Morris, D.L., and Morris, C.T. (1939) Glycogen in the seed of *Zea mays* (variety golden bantam). Journal of Biological Chemistry, 130(2), 535-544.
Thompson, D.B. (2000) . On the non-random nature of amylopectin branching. Carbohydr. Res. 43: 223-239.
Bell, D. J., & Young, F. G. (1934). Observations on the chemistry of liver glycogen. The Biochemical Journal, 28(3), 882-9.
Bueding, E. and Orrell, S. A. (1961). Sedimentation coefficient distributions of cold water-extracted glycogens of Fasciola hepatica. J Biol Chem., 236:2854-7.

(Continued)

*Primary Examiner* — Yanzhi Zhang
(74) *Attorney, Agent, or Firm* — Norton Rose Fulbright Canada LLP

(57) ABSTRACT

A composition of phytoglycogen nanoparticles purified from a phytoglycogen-containing plant material is provided. The composition of phytoglycogen nanoparticles is monodisperse. A method of isolating the composition from phytoglycogen-containing plant materials is provided that includes steps of microfiltration and ultrafiltration, but avoids the use of chemical, enzymatic or thermo treatments that degrade the phytoglycogen material.

30 Claims, 4 Drawing Sheets

(56) References Cited

FOREIGN PATENT DOCUMENTS

| WO | 2011062999 A2 | * | 5/2011 | ............ A23L 1/035 |
| WO | 2011062999 A2 | | 5/2011 | |
| WO | 2012109121 A1 | | 8/2012 | |
| WO | 2013019977 A2 | | 2/2013 | |
| WO | 2013/056227 | * | 4/2013 | ............ A23L 1/035 |
| WO | 2013056227 A2 | | 4/2013 | |
| WO | 2013158992 A1 | | 10/2013 | |
| WO | 2014172785 A1 | | 10/2014 | |

OTHER PUBLICATIONS

Dinuzzo, M. (2013). Kinetic analysis of glycogen turnover: relevance to human brain (13) C-NMR spectroscopy. Journal of cerebral blood flow and metabolism. Journal of Cerebral Blood Flow & Metabolism, 33(10): 1540-1548.
Manners, D.J. (1991). Recent developments in our understanding of glycogen structure. Carbohydrate Polymers, 16(1):37-82.
Meléndez, R. et al (1999). The fractal structure of glycogen: A clever solution to optimize cell metabolism. Biophysical Journal, 77(3), 1327-1332.
Meléndez, R. et al (1997). How did glycogen structure evolve to satisfy the requirement for rapid mobilization of glucose? A problem of physical constraints in structure building. Journal of Molecular Evolution, 45(4), 446-455.
Meléndez, R. et al (1998). Physical constraints in the synthesis of glycogen that influence its structural homogeneity: a two-dimensional approach. Biophysical Journal, 75(1), 106-114.
Meléndez-Hevia, E. et al (1993). Optimization of molecular design in the evolution of metabolism: the glycogen molecule. Biochem J, 295(2):477-483.
Orrell, S. A. & Bueding, E. (1964). A comparison of products obtained by various procedures used for the extraction of glycogen. J. Biol. Chem., 239(12), 4021-4026.
Miao, M. et al (2014). Structure and digestibility of endosperm water-soluble $\alpha$-glucans from different sugary maize mutants. Food Chemistry, 143, pp. 156-162.
Miao, M. et al (2014). Structure and physicochemical properties of octenyl succinic esters of sugary maize soluble starch and waxy maize starch. Food Chemistry, 151, 154-160.
Ryu, J. H. et al (2009). Comparative structural analyses of purified glycogen particles from rat liver, human skeletal muscle and commercial preparations. International Journal of Biological Macromolecules, 45(5), 478-482.
Kajiura, H. et al (2008). A novel enzymatic process for glycogen production. Biocatalysis and Biotransformation, 26 (1-2), 133-140.
Stetten, M.R. et al (1958). A comparison of the glycogens isolated by acid and alkaline procedures. J. Biol. Chem. 232: 475.
Whistler, R.L., and Bemiller J.N. (1962). Extraction of glycogen with dimethyl sulfoxide. Archives of Biochemistry and Biophysics, 98(1):120-123.
Anderson, B.A. et al (2003). Use of phytoglycogen extracted from corn to increase the bowl-life of breakfast cereal. Journal of Food Process Engineering, 26(3), 315-322.
Asaoka, M. et al (1985). Structure and properties of endosperm starch and water soluble polysaccharides from sugary mutant of rice (*Oryza sativa* L.). Starch/Stärke, 37: 364-366.
Black, R.C. et al (1966). Genetic interactions affecting maize phytoglycogen and the phytoglycogen-forming branching enzyme. Genetics 53, 661-668.
Boyer, C. D., and Liu, K. C. (1983). Starch and water soluble polysaccharides from sugary endosperm of sorghum. Phytochemistry 22:2513-2515.
Burton, R. A. et al (2002). Starch granule initiation and growth are altered in barley mutants that lack isoamylase activity. Plant Journal, 31(1), 97-112.
Curá, J. A. and Krisman, C. R. (1990). Cereal Grains: A Study of their $\alpha$-1,4-$\alpha$-1,6 Glucopolysaccharide Composition. Starch/Stärke, 42(5), pp. 171-175.

Curá, J. A. and Krisman, C. R. (1995). Maize Mutants. Part: Studies on their Starch Components. Starch/Stärke, 47(6), pp. 210-213.
Dinges, J. R. et al (2001). Molecular structure of three mutations at the maize sugary1 locus and their allele-specific phenotypic effects. Plant Physiology, 125(3), 1406-1418.
Fujita, N. et al (2003). Antisense inhibition of isoamylase alters the structure of amylopectin and the physicochemical properties of starch in rice endosperm. Plant Cell Physiol 44 (6): 607-618.
Gonzales, J. W. et al (1976). Carbohydrate and enzymic characterization of a high sucrose sugary inbred line of sweet corn. Plant Physiol, 58(1), 28-32.
James, M. G. (1995). Characterization of the maize gene sugary1, a determinant of starch composition in kernels. The Plant Cell, 7(4), 417-429.
Inouchi, N. et al (1983) Development Changes in Fine Structure of Starches of Several Endosperm Mutants of Maize. Starch-Stärke, 35(11), 371-376.
Nakano, A. et al (1997). Glycogen-Surfactant Complexes: Phase Behavior in a Water/Phytoglycogen/Sodium Dodecyl Sulfate (SDS) System. Biosci Biotechnol Biochem., 61(12):2063-8.
Nakano, A., et al (1997). Dispersion Stability of Phytoglycogen in Water/Phytoglycogen/Various Nonionic Surfactant Systems: Effect of Hydrophile-Lipophile Balance (HLB) of Nonionic Surfactants. Bulletin of the Chemical Society of Japan, 70(12), 2943-2949.
Pan, D., & Nelson, O. E. (1984). A debranching enzyme deficiency in endosperms of the sugary-1 mutants of maize. Plant Physiology, 74(2), 324-8.
Peat, S.B. et al (1956). The soluble polyglucose of sweet corn (*Zea mays*). J. Chem. Soc., 1956, 2317-2322.
Powell, P. O. et al (2014). Extraction, isolation and characterisation of phytoglycogen from su-1 maize leaves and grain. Carbohydrate Polymers, 101(1), 423-431.
Powell, P.O. et al (2015). Acid Hydrolysis and Molecular Density of Phytoglycogen and Liver Glycogen Helps Understand the Bonding in Glycogen $\alpha$ (Composite) Particles. PLOS ONE, 10(1371), 1-20.
Putaux, J. L. et al (1999). Ultrastructural aspects of phytoglycogen from cryo-transmission electron microscopy and quasi-elastic light scattering data. International Journal of Biological Macromolecules, 26(2-3), 145-50.
Stetten, M.R. et al (1956). Metabolic inhomogeneity of glycogen as a function of molecular weight. J. Biol. Chem. 222:587-599.
Tateishi, K., & Nakano, A. (1997). Effects of degree of branching on dispersion stability of phytoglycogen in aqueous solution. Bioscience, Biotechnology, and Biochemistry, 61(3), 455-458.
Verhoeven, T. et al (2004). Isolation and characterisation of novel starch mutants of oats. Journal of Cereal Science, 40(1), 69-79.
Wong, K-S et al (2003). Structures and Properties of Amylopectin and Phytoglycogen in the Endosperm of sugary-1 Mutants of Rice. Journal of Cereal Science, 37(2), 139-149.
Yun, S. H. & Matheson, N. K. (1993). Structures of the amylopectins of waxy, normal, amylose-extender, and wx: ae genotypes and of the phytoglycogen of maize. Carbohydrate Research, 243(2), 307-321.
Zeeman, S. C. et al (1998). A mutant of Arabidopsis lacking a chloroplastic isoamylase accumulates both starch and phytoglycogen. The Plant Cell, 10(10), 1699-1712.
Bi, L. et al (2011). Carbohydrate nanoparticle-mediated colloidal assembly for prolonged efficacy of bacteriocin against food pathogen. Biotechnology and Bioengineering, 108(7), 1529-1536.
Bi, L. et al (2011). Designing carbohydrate nanoparticles for prolonged efficacy of antimicrobial peptide. Journal of Controlled Release, 150(2), 150-156.
Morris, D.L., and Morris, C.T. (1939). Glycogen in sweet corn. Science (n.s.) 90(2332): 238-239.
Chen, H. et al (2015). Particulate structure of phytoglycogen studied using $\beta$-amylolysis. Carbohydrate Polymers, 132:582-588.
Huang, L., & Yao, Y. (2011). Particulate structure of phytoglycogen nanoparticles probed using amyloglucosidase. Carbohydrate Polymers, 83(4), 1665-1671.
Scheffler, S. L. et al (2010). In vitro digestibility and emulsification properties of phytoglycogen octenyl succinate. Journal of Agricultural and Food Chemistry, 58(8), 5140-5146.

(56) References Cited

OTHER PUBLICATIONS

Scheffler, S.L. et al (2010). Phytoglycogen octenyl succinate, an amphiphilic carbohydrate nanoparticle, and ε-polylysine to improve lipid oxidative stability of emulsions. Journal of Agricultural and Food Chemistry, 58(1), 660-667.

Shin, J.E. et al (2008). Glucose release of water-soluble starch-related α-glucans by pancreatin and amyloglucosidase is affected by the abundance of α-1,6-glucosidic linkages. Journal of Agricultural and Food Chemistry, 56(22), 10879-10886.

Yao, Y. (2011). Structure and function of dendrimer-like polysaccharides, phytoglycogen and its derivatives. Polymer Preprints, 52(2), 195-196.

* cited by examiner

FIGURE 2.

| Measurement Parameters: | | | |
|---|---|---|---|
| Temperature | = 25.0 deg. C | Runs Completed | = 3 |
| Liquid | = Water | Run Duration | = 00:00:30 |
| Viscosity | = 0.890 cP | Total Elapsed Time | = 00:01:30 |
| Ref.Index Fluid | = 1.330 | Average Count Rate | = 144.1 kcps |
| Angle | = 90.00 | Ref.Index Real | = 1.500 |
| Wavelength | = 657.0 nm | Ref.Index Imag | = 0.000 |
| Baseline | = Auto (Slope Analysis) | Dust Filter Setting | = 50.00 |

NK199 (Combined)

Effective Diameter: 63.0 nm

Polydispersity: 0.053

Baseline Index: 8.8/100.00%

Elapsed Time: 00:01:30

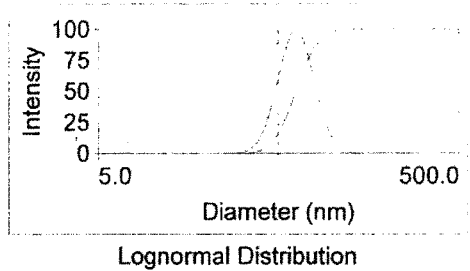

Lognormal Distribution

| Measurement Parameters: | | | |
|---|---|---|---|
| Temperature | = 25.0 deg. C | Runs Completed | = 3 |
| Liquid | = Water | Run Duration | = 00:00:30 |
| Viscosity | = 0.890 cP | Total Elapsed Time | = 00:01:30 |
| Ref.Index Fluid | = 1.330 | Average Count Rate | = 359.3 kcps |
| Angle | = 90.00 | Ref.Index Real | = 1.500 |
| Wavelength | = 657.0 nm | Ref.Index Imag | = 0.000 |
| Baseline | = Auto (Slope Analysis) | Dust Filter Setting | = 50.00 |

Phytospherix v.113U-01 (Combined)

Effective Diameter: 83.0 nm

Polydispersity: 0.081

Baseline Index: 8.6/ 98.53%

Elapsed Time: 00:01:30

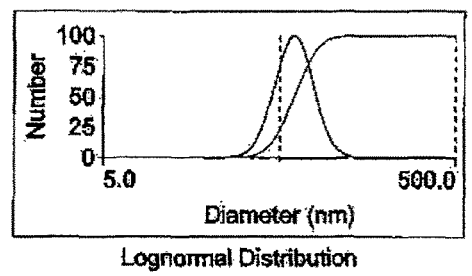

Lognormal Distribution

FIGURE 3.

PHYTOGLYCOGEN NANOPARTICLES AND METHODS OF MANUFACTURE THEREOF

CROSS-REFERENCE TO RELATED APPLICATIONS

This application claims priority from U.S. patent application 61/816,686 filed on Apr. 26, 2013 and its contents is incorporated herewith in its entirety.

TECHNICAL FIELD

This invention relates to phytoglycogen nanoparticles and methods of producing phytoglycogen nanoparticles.

BACKGROUND OF THE ART

Phytoglycogen and glycogen are polysaccharides of glucose composed of α-1,4-glucan chains, highly branched via α-1,6-glucosidic linkages, which function as energy storage mediums in plant and animal cells. Glycogen is present in animal tissue in the form of dense particles with diameters of 20-200 nm. Glycogen is also found to accumulate in microorganisms, e.g., bacteria and yeasts. Phytoglycogen is a polysaccharide that is similar to glycogen, both in terms of its structure and physical properties and originates in plants.

Glycogen and phytoglycogen are considered "highly polydisperse" or heterogeneous materials. Glycogen typically has a molecular weight between $10^6$ and $10^8$ Daltons with a corresponding large polydispersity for known preparations. Transmission electron microscopy (TEM) observations of animal and plant tissues and extracted glycogen/phytoglycogen preparations have revealed the particulate nature of these polysaccharides. Commonly reported glycogen or phytoglycogen particle diameters are in the range of 20-300 nm and have either continuous or multimodal size distribution. Small, 20-30 nm, particles are termed β-particles and large, 100-300 nm—α-particles. The α-particles are considered to be composed of β-particles as a result of aggregation or clustering [1].

Various methods have been developed to isolate glycogen and phytoglycogen from living organisms, most often for the purpose of quantifying the amount of total glycogen accumulated in biological samples, and, infrequently, for the purpose of using the glycogen as a product in applications.

The most frequently used method is extraction from animal tissues, particularly from marine animals, especially mollusks, because of their ability to accumulate glycogen. For example, U.S. Pat. No. 5,734,045 discloses a process for the preparation of protein-free glycogen from mussels by using hot alkali extraction, following neutralization and treatment of the resulting solution with cationic resins. Glycogen can also be produced via fermentation of yeasts as described, for example, in patent application WO/1997/021828. U.S. Pat. No. 7,670,812 describes a process for the biosynthetic production of glycogen-like polysaccharides by exposing a mixture of enzymes to low molecular weight dextrins. Sweet corn and sweet rice can be used as a source of glycogen; see, for example, patent application EP0860448B1, which describes a process of isolating glycogen from the kernels of sweet rice.

The main steps of glycogen/phytoglycogen isolation typically include: biomass disintegration via pulverization/grinding/milling etc.; glycogen extraction into water phase; separation of insoluble solid particles via filtration and/or centrifugation; elimination of finely dispersed or solubilized lipids, proteins and low molecular weight contaminates; and concentration and drying.

To increase the yield of glycogen in the second extraction step, extraction is often performed at elevated temperatures and/or using alkaline or acidic solutions. Such procedures include initial treatment of ground biological material with hot concentrated (20-40%) solution of alkali [2, 3], cold acids [4] or boiling water [5].

The procedures used in the conventional methods of glycogen isolation/purification result in considerable hydrolysis of the glycogen structure, with significant increases of lower molecular weight products and chemical alteration of the molecule.

Various milder extraction procedures have been developed, such as cold water extraction [6], and resulting products were claimed to be close representation of natural state of the glycogen. However, known glycogen preparations produced by cold water extraction method are highly polydisperse [7,1].

Various methods are known for performing the step of purifying crude glycogen extract from finely dispersed proteins, lipids, nucleic acids, and other polysaccharides. Protein and nucleic acids can be removed via selective precipitation with deoxycholate (DOC) trichloroacetic acid (TCA), polyvalent cations, and/or enzymatic (protease, nuclease) treatment. Also methods of removing proteins by salting them out (e.g., with ammonium sulfate), or by ion-exchange have been used. Another common method of protein removal is thermal coagulation, normally at 65-100° C., following by centrifugation or filtration. Autoclaving (121° C. at 1 atm) has also been used to coagulate proteins in phytoglycogen extract [8]. Furthermore, proteins and lipids can be removed with phenol-water extraction.

International patent application publication no. WO 2013/019977 (Yao) teaches a method for obtaining extracts that include phytoglycogen that includes ultrafiltration, but also subjecting the aqueous extract to enzymatic treatment that degrades both phytoglycogen as well as other polysaccharides. Yao provides a method to reduce viscosity of phytoglycogen material by subjecting it to beta-amylolysis, i.e., enzymatic hydrolysis using beta-amylase. The "purified phytoglycogen" materials yielded by the methods of Yao include not only phytoglycogen, but derivatives of phytoglycogen, including beta-dextrins and the digestion products of other polysaccharides. The method of Yao further involves heating the extract to 100° C. (see Yao Example 1).

U.S. Pat. No. 5,895,686 discloses a method for extracting phytoglycogen from rice by water or a water-containing solvent (at room temperature) and the removal of proteins by thermal denaturation and TCA precipitation. The product has a multimodal molecular weight distribution, with correspondingly high polydispersity, and large water solution viscosities. These properties can be attributed to the presence of substantial amounts of amylopectin and amylose in glycogen preparations from plant material, but also to glycogen degradation during the glycogen extraction process.

U.S. Pat. Nos. 5,597,913 and 5,734,045 describe procedures that result in glycogen that is substantially free of nitrogenous compounds and reducing sugars as an indication of its purity from proteins and nucleic acids. These patents teach the use of boiling of the selected tissues in solutions of high pH.

United States patent application publication no. United States 20100272639 A1, assigned to the owner of the present invention, provides a process for the isolation of glycogen from bacterial and shell fish biomass. Bacteria is taught as preferred since the process can be conducted to yield a biomass that does not have other large molecular weight polysaccharides such as amylopectin and amylose and is free of pathogenic bacteria, parasites, viruses and prions associated with shell-fish or animal tissue. The processes disclosed generally include the steps of cell disintegration by French pressing, or by chemical treatment; separation of insoluble cell components by centrifugation; elimination of proteins and nucleic acids from cell lyzate by enzymatic treatment followed by dialysis which produces an extract containing crude polysaccharides and lypopolysaccharides (LPS) or, alternatively, phenol-water extraction; elimination of LPS by weak acid hydrolysis, or by treatment with salts of multivalent cations, which results in the precipitation of insoluble LPS products; and purification of the glycogen enriched fraction by ultrafiltration and/or size exclusion chromatography; and precipitation of glycogen with a suitable organic solvent or a concentrated glycogen solution can be obtained by ultrafiltration or by ultracentrifugation; and freeze drying to produce a powder of glycogen. Glycogen isolated from bacterial biomass was characterized by MWt $5.3\text{-}12.7 \times 10^6$ Da, had particle size 35-40 nm in diameter and were monodisperse (PDI=$M_n/M_w$=1.007-1.03).

BRIEF SUMMARY

In one embodiment, there is described a composition of phytoglycogen nanoparticles obtained from a phytoglycogen-containing plant material, the phytoglycogen nanoparticles having a polydispersity index of less than 0.3 as measured by dynamic light scattering (DLS). In one embodiment, the phytoglycogen nanoparticles have a polydispersity index of less than 0.2 as measured by DLS. In one embodiment, the phytoglycogen nanoparticles have a polydispersity index of less than 0.1 as measured by DLS.

In one embodiment, the phytoglycogen nanoparticles have an average particle diameter of between about 30 nm and about 150 nm. In one embodiment, the phytoglycogen nanoparticles have an average particle diameter between about 60 nm and 110 nm.

In one embodiment, the composition based on dry weight includes more than 80% phytoglycogen nanoparticles having an average particle diameter of between about 30 nm and 150 nm. In one embodiment, the composition based on dry weight includes more than 90% phytoglycogen nanoparticles having an average particle diameter of between about 30 nm and 150 nm. In one embodiment, the composition based on dry weight includes more than 99% phytoglycogen nanoparticles having an average particle diameter of between about 30 nm and 150 nm. In one embodiment, the composition based on dry weight includes more than 80% phytoglycogen nanoparticles having an average particle diameter of between about 60 nm and 110 nm. In one embodiment, the composition based on dry weight includes more than 90% phytoglycogen nanoparticles having an average particle diameter of between about 60 nm and 110 nm. In one embodiment, the composition based on dry weight includes more than 99% phytoglycogen nanoparticles having an average particle diameter of between about 60 nm and 110 nm.

In one embodiment, the phytoglycogen-containing plant material is obtained from corn, rice, barley, sorghum or a combination thereof. In one embodiment, the phytoglycogen-containing plant material is standard type (su) or surgary extender (se) type sweet corn. In one embodiment, the phytoglycogen-containing plant material is obtained from milk stage or dent stage corn kernels.

In one embodiment, the composition is a powder. In another embodiment, the composition is an aqueous dispersion of the phytoglycogen nanoparticles.

Also described herein is a method of producing monodisperse phytoglycogen nanoparticles comprising: a. immersing disintegrated phytoglycogen-containing plant material in water at a temperature between about 0 and about 50° C.; b. subjecting the product of step (a.) to a solid-liquid separation to obtain an aqueous extract; c. passing the aqueous extract of step (b.) through a microfiltration material having a maximum average pore size of between about 0.05 and 0.15 µm; and d. subjecting the filtrate from step c. to ultrafiltration to remove impurities having a molecular weight of less than about 300 kDa to obtain an aqueous composition comprising monodisperse phytoglycogen nanoparticles.

In one embodiment of the method, the phytoglycogen-containing plant material is a cereal. In one embodiment, the cereal is corn, rice, barley, sorghum or a mixture thereof. In one embodiment, the phytoglycogen-containing plant material is standard type (su) or surgary extender (se) type sweet corn. In one embodiment, the phytoglycogen-containing plant material is milk stage or dent stage kernel of standard type (su) or surgary extender (se) type sweet corn.

In one embodiment, the method includes step (e.) subject the aqueous composition comprising monodisperse phytoglycogen nanoparticles to enzymatic treatment using amylosucrose, glycosyltransferase, branching enzymes or any combination thereof.

In one embodiment, the method includes step (e.1) drying the aqueous composition comprising monodisperse phytoglycogen nanoparticles to yield a dried composition of substantially monodisperse phytoglycogen nanoparticles.

In one embodiment, the methods includes adding an adsorptive filtration aid prior to step c or step d. In one embodiment, the adsorptive filtration aid is a diatomaceous earth.

In one embodiment, the solid-liquid separation step involves agitating the product of step (a.) for a period of 10 to 30 minutes.

In one embodiment of the method, the ultrafiltration of step (d.) removes impurities having a molecular weight less than 500 kDa.

In one embodiment, step c. comprises passing the aqueous extract of step (b.) through (c.1) a first microfiltration material having a maximum average pore size between about 10 µm and about 40 µm; (c.2) a second microfiltration material having a maximum average pore size between about 0.5 µm and about 2.0 µm, and (c.3) a third microfiltration material having a maximum average pore size between about 0.05 and 0.15 µm.

In one embodiment, the method further includes centrifuging the product of step b.

Also described herein are compositions of substantially monodisperse nanoparticles produced according to the methods described.

In one embodiment, the compositions described herein are used as film-forming agents. In one embodiment, the compositions described herein are used as drug-delivery agents.

BRIEF DESCRIPTION OF THE DRAWINGS

FIG. 2 shows particle size distribution of the phytoglycogen isolated according to EXAMPLE 1 using DLS.

FIG. 3 shows particle size distribution of the phytoglycogen isolated according to EXAMPLE 2 using DLS.

DETAILED DESCRIPTION

Figure 1:
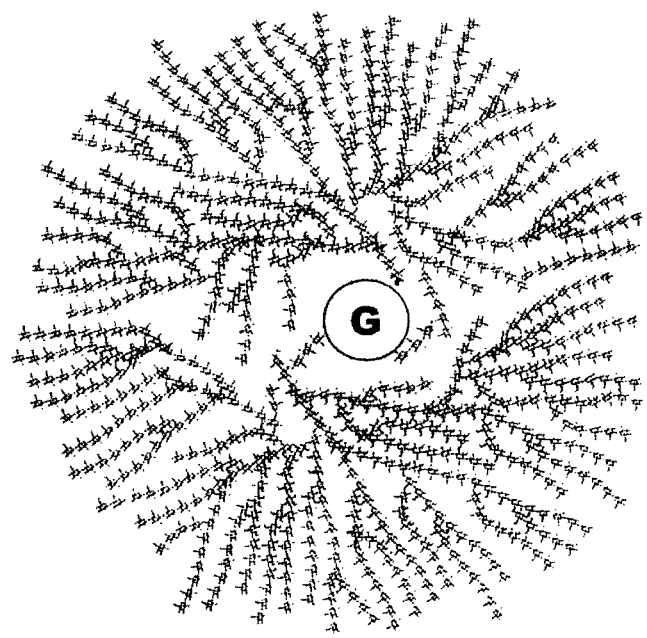
FIG. 1 is a schematic drawing of a phytoglycogen nanoparticle.

"Phytoglycogen" as used herein refers to a nanoparticle of α-D glucose chains obtained from plant material, having an average chain length of 11-12, with 1→4 linkage and branching point occurring at 1→6 and with a branching degree of about 6% to about 13%.

In one embodiment, there is provided a composition of monodisperse nanoparticles of a high molecular weight glucose homopolymer. In one embodiment, there is provided a composition of monodisperse phytoglycogen nanoparticles.

The polydispersity index (PDI), determined by dynamic light scattering (DLS) technique, is defined as the square of the ratio of standard deviation to mean diameter: $PDI=(\sigma/d)^2$. Also, PDI can be expressed through the distribution of the molecular weight of polymer, and defined as the ratio of $M_w$ to $M_n$, where $M_w$ is the weight-average molar mass and $M_n$ is the number-average molar mass (hereafter this PDI measurement is referred to as PDI*). In the first case, monodisperse material has PDI close to zero (0.0), and in the second—1.0. In one embodiment, there is provided a composition of phytoglycogen nanoparticles having a PDI of less than about 0.3, less than about 0.2, less than about 0.15, less than about 0.10, less than 0.07 or less than 0.05 as measured by DLS. In one embodiment, there is provided a composition of phytoglycogen nanoparticles having a PDI* of less than about 1.3, less than about 1.2, less than about 1.15, less than about 1.10, or less than 1.05 as measured by SEC MALS.

Monodispersity is advantageous for a number of reasons, including that surface modification and derivatization occurs much more predictably if the nanoparticles of a composition are monodisperse. Size also affects the distribution and accumulation of the nanoparticles in biological tissues, as well as pharmacokinetics. Furthermore, narrow size distribution is critical for such applications as diagnostic probes, catalytic agents, nanoscale thin films, and controlled rheology.

Nanoparticle size, including distributions (dispersity) and average values of the diameter, can be measured by methods known in the art. These primarily include DLS and microscopy techniques, e.g. TEM, and atomic force microscopy.

In one embodiment, there is provided a monodisperse composition of phytoglycogen nanoparticles having an average particle diameter of between about 30 and about 150 nm, in one embodiment, between about 60 nm and about 110 nm. These nanoparticles are individual particles as opposed to clustered α-particles seen in prior compositions.

In one embodiment, the phytoglycogen nanoparticles are produced from a cereal. In one embodiment, the phytoglycogen is produced from corn, rice, barley, sorghum or a mixture thereof.

Varieties used must be phytoglycogen-containing. Whether a variety contains phytoglycogen can be readily determined by those of skill in the art using known techniques. In addition, for many varieties, published literature identifies whether a variety contains phytoglycogen.

In one embodiment, the composition is obtained from sweet corn (*Zea mays* var. saccharate and *Zea mays* var. rugosa). In one embodiment, the sweet corn is of standard (su) type or sugary enhanced (se) type.

In one embodiment, the composition is obtained from dent stage or milk stage kernels of sweet corn.

In one embodiment, the monodisperse composition of phytoglycogen nanoparticles is substantially pure. In one embodiment, the composition based on dry weight is composed of at least about 80%, at least about 85%, at least about 90%, at least about 95% phytoglycogen nanoparticles having a diameter size of between about 30 nm and about 150 nm. In another embodiment, the composition based on dry weight is composed of at least about 99% phytoglycogen nanoparticles having a diameter size between about 30 nm and about 150 nm. In one embodiment, the composition based on dry weight is composed of at least about 80%, at least about 85%, at least about 90%, at least about 95% phytoglycogen nanoparticles having a diameter size of between about 60 nm and about 110 nm. In another embodiment, the composition based on dry weight is composed of at least about 99% phytoglycogen nanoparticles having a diameter size between about 60 nm and about 110 nm.

In one embodiment, the composition is substantially free of other polysaccharides. In one embodiment, the composition contains less than about 10% of other polysaccharides. In one embodiment, the composition contains less than about 5% other polysaccharides. In one embodiment, the composition contains less than about 1% of other polysaccharides.

Glycogen

Glycogen and phytoglycogen consists of linear chains of glucose residues connected by α-1→4-glycosidic bonds, with branches that are attached through α-1→6-glycosidic bonds. Chemical analysis of mammalian glycogen from different sources suggests that its average chain length is ~13 residues [9]. As shown in FIG. 1, an accepted model for glycogen structure has inner chains, which would normally contain two branch points, and outer chains, which are unbranched. The entire tree-shaped polymer is rooted in a single molecule of the protein glycogenin (G).

Density of the glycogen molecule increases exponentially with the number of tiers. It has been calculated that addition of a 13th tier to a glycogen molecule would add an impossible density of glucose residues, making 12 tiers a theoretical maximum [9]. An important feature is that the outermost tier of any molecule completely formed in this way would contain ~45-50% of the total glucose residues of the molecule as unbranched A-chains, while the first eight inner tiers only contain ~5% of the total glucose. Therefore a full-size glycogen molecule in this model would consist of 12 tiers, for a total of ~53000 glucose residues, a molecular mass of ~107 kDa and a diameter of ~25 nm. Although predominantly composed of glucose residues, glycogen may contain other trace constituents, notably glucosamine and phosphate [1]. Mathematical modeling showed that the structural properties of the glycogen molecule depend on three parameters, namely, the branching degree (r), the number of tiers (t), and the number of glucose residues in each chain (gc) [9,10,11,12,13].

Despite the spherical shape of the glycogen molecule suggested by the mechanism of growth, on growing the molecule beyond a certain limit, it loses structural homogeneity, as the branching degree and the chain length degenerate in the last tiers.

Phytoglycogen

Although glycogen and phytoglycogen have very similar structure there is a principal difference in the functional purpose of these polysaccharides. Glycogen in animals and bacteria is meant to serve as a short-term "fuel" storage optimized for the fast turnover.

In plants the main energy source is starch, which is stored in leaves, stems, seeds, roots, etc. In contrast to glycogen, starch is a long-term energy strategy that allows the plant to survive during adverse climate situations. Starch contains two types of polyglucans: amylopectin (which is highly branched) and amylose (which is almost linear with few branches. There are large variations in the contents of the two components in starches from different sources, but amylopectin is commonly considered the major component in storage starch and accounts for about 65-85% by weight.

Amylopectin has a defined structure composed of tandem linked clusters (approximately 9-10 nm each in length) where linear α-1,4-glucan chains are highly and regularly branched via α-1,6-glucosidic linkages The semi-crystalline structure formed by amylopectin branches is of biological and economic importance, as this structure allows plants to store carbon at high density (~1.6 g cm-3) [14].

Amylopectin is synthesized by multiple isoforms of four classes of enzymes: soluble starch synthase (SS), starch branching enzyme (BE), ADPglucose pyrophosphorylase, and starch debranching enzyme (DBE). These are the same 4 classes of enzymes that are involved in glycogen synthesis.

This explains the similarity between amylopectin and glycogen structure: both are α-1,4-polyglucans with α-1,6-branching. However, the average chain length ($g_c$) in amylopectin is 20-25, about twice longer than in glycogen, while the degree of branching (r) is about 1.5-2 times lower.

Mutation in isoamylase (ISA) and, therefore, deficiency in debranching activity, results in partial substitution of amylopectin with phytoglycogen. Most common examples of such phytoglycogen accumulating plants are sugary 1 (su) mutants of corn, rice and other cereals.

Phytoglycogen structurally is similar to glycogen, having average chain length 11-12 and similar degree of branching and typically has a molecular weight between $10^6$-$10^8$ Da. However, reported larger particle sizes than glycogen suggest lower degree of branching and/or lower structural homogeneity. Lower structural homogeneity of phytoglycogen is not unexpected, considering that glycogen is a highly optimized metabolic product, while phytoglycogen is a result of a derangement in amylopectin synthesis.

The present inventors have experimentally determined that the reported polydispersity of compositions of phytoglycogen is in fact partly due to destructive isolation methods, and observed polydispersity can further arise from the presence of finely dispersed contaminants such as proteins, lipids and other polysaccharides. Using methods described herein, the present inventors have produced monodisperse compositions of phytoglycogens.

Method of Producing Monodisperse Phytoglycogen

As discussed above, the main steps of glycogen/phytoglycogen isolation typically include: 1. Biomass disintegration via pulverization/grinding/milling etc.; 2. Glycogen extraction into water phase; 3. Separation of insoluble solid particles (solids) via filtration and/or centrifugation; 4. Elimination of finely dispersed or solubilized lipids, proteins and low molecular weight contaminates; and 5. Concentration and Drying. Some operations can be combined e.g., milling and extraction.

In one embodiment, a method of producing monodisperse phytoglycogen nanoparticles includes:

a. immersing disintegrated plant material in water at a temperature between about 0° C. and about 50° C.; in one embodiment, between about 4° C. and about 20° C.;

b. subjecting the product of step (a.) to a solid-liquid separation to obtain an aqueous extract;

c. filtering the aqueous extract of step (b.), suitably in a multistage filtration process, but at least through a microfiltration material having a maximum average pore size of about 0.1 μm;

d. subjecting the filtrate from step c. to ultrafiltration to remove impurities having a molecular weight of less than about 300 kDa, in one embodiment, less than about 400 kDa, in one embodiment, less than about 500 kDa, to obtain a composition comprising monodisperse phytoglycogen nanoparticles.

In one embodiment, the method further includes centrifuging the product of step b.

The aqueous dispersion can then be dried to yield a composition of substantially monodisperse phytoglycogen nanoparticles.

In one embodiment, the plant material is a cereal. In one embodiment, the plant material is corn, rice, barley, sorghum or mixtures thereof. In one embodiment, the plant material is the kernel of sweet corn (*Zea mays* var. *saccharata* and *Zea mays* var. *rugosa*). In one embodiment, milk stage or dent stage maturity kernel of sweet corn is used.

The yield of phytoglycogen is in various embodiments, between about 5% and 50%, between about 10% and about 50%, between about 20% and 50%, between about 30% and about 50%, between about 40% and about 50%, between about 10% and about 40%, between about 20% and 40%, between about 30% and about 40% of the dry weight of the plant material. The exact yield of phytoglycogen will depend on the plant material used, including the variety and stage of maturity. In the case of corn, the inventors have obtained yields in the range of 35-40% of the kernel dry weight for milk stage kernel maturity and 20-30% for the dent stage maturity. These yields of monodisperse phytoglycogen were unexpected, given the high polydispersity of previously reported phytoglycogen.

Methods of preparing disintegrated plant material are known to those skilled in the art. Methods of biomass disintegration include grinding, milling or pulverizing of biomaterial. The plant materials are suitably disintegrated to an average particle size of less than about 0.5 mm.

In one embodiment, the cold water extraction is performed by moderate agitation for 10-30 min. In one embodiment, the cold water extraction is performed at a temperature of between about 0° C. and about 50° C. In one embodiment, the cold water extraction is performed at a temperature of between about 4° C. and about 20° C. The optimal period of agitation, temperature and agitation rate depend on the nature of the disintegrated biomass, and determining the same is within the purview of a person of skill in the art.

The aqueous extract that results from the cold water extraction is centrifuged to separate out crude non-soluble solids. Suitably, the extract is optionally centrifuged at about 3,000 to about 6,000×g. Suitably a further centrifugation is performed by centrifugation at about 6,000 to about 12,000× g, which separates in part finely dispersed proteins and lipids from the crude phytoglycogen extract.

Centrifugation is followed by filtration of the supernatant. As described herein, a multistage filtration and ultrafiltration are performed, which surprisingly has been found to eliminate most of the proteins, lipids and contaminating polysaccharides, including amylose and amylopectin, without any chemical, enzymatic or thermo treatment, thereby yielding a composition of monodisperse phytoglycogen nanoparticles. Microfiltration is suitably performed in stages with a final media pore size of 0.1 μm. In one embodiment, microfiltration is performed successively with media pore sizes of between a) in one embodiment, about 5 μm and about 50 μm, in one embodiment, between about 10 μm and about 40 μm, in one embodiment, between about 15 μm and about 35 μm, in one embodiment, between about 20 μm and about 30 μm, and in one embodiment, about 25 μm; b) in one embodiment between about 0.5 μm and about 2.0 μm, in one embodiment, about 1.0 μm; and c) in one embodiment, between about 0.05 μm and about 0.15 μm, in one embodiment, 0.1 μm. In one embodiment, an adsorptive filtration aid such as diatomaceous earth can be added to phytoglycogen extract prior to centrifugation. In one embodiment, the adsorptive filtration aid is used in an amount of about 2-10% wt/vol, in one embodiment, between about 3-5% wt/vol.

The final filtrate from the microfiltration is subject to ultrafiltration, which removes low molecular weight contaminants therefrom including salts, proteins and sugars e.g. dextrins, glucose, sucrose or maltose. Ultrafiltration is suitably performed by Cross Flow Filtration (CFF) with a molecular weight cut off (MWCO) of about 300 to about 500 kDa.

Various methods of microfiltration and ultrafiltration are known to those of skill in the art and any suitable method may be employed.

Optionally, following ultrafiltration the aqueous dispersion containing phytoglycogen can be subject to enzymatic treatment to reduce polydispersity. Suitably, it can be treated with amylosucrose, glycogen synthase, glycosyltransferase and branching enzymes or any combination thereof. However, enzymes that digest amylopectin and amylose (e.g. beta-amylase) should be avoided as they will yield a solution of polyglucans variously degraded, rather than a purified composition of phytoglycogen nanoparticles.

Phytoglycogen dispersions can be concentrated (up to 30%) by the process of CFF ultrafiltration. Alternatively, following CFF ultrafiltration, phytoglycogen can be precipitated with a suitable organic solvent such as acetone, methanol, propanol, etc., preferably ethanol. The method further includes drying the phytoglycogen extract, suitably by spray drying or freeze drying. Various standard concentrating and/or drying methods, such as use of a falling film evaporator, a rising film evaporator, spray drying, freeze drying, drum drying, or combinations thereof, etc., can be used to dehydrate the phytoglycogen dispersion and/or collect the solid form of phytoglycogen product.

As shown in the Examples, resulting phytoglycogen material is characterized by a particle diameter of between 30 nm and 150 nm, depending on the starting plant material used, with a polydispersity index as low as 0.07 as measured by DLS.

The key to ensure high purity materials and its monodispersity is a combination of fine microfiltration and ultrafiltration.

Chemical Functionalization of the Nanoparticles

Embodiments of the present invention include nanoparticles and molecules with chemically functionalized surface and/or nanoparticles conjugated with a wide array of molecules. Chemical functionalization is known in the art of synthesis. See, for example, March, *Advanced Organic Chemistry*, 6th Ed., Wiley, 2007. Functionalization can be carried out on the surface of the particle, or on both the surface and the interior of the particle, but the structure of the glycogen molecule as a singlebranched homopolymer as described above is maintained.

Such functionalized surface groups include, but are not limited to, nucleophilic and electrophilic groups, acidic and basic groups, including for example carbonyl groups, amine groups, thiol groups, carboxylic or other acidic groups. Amino groups can be primary, secondary, tertiary, or quaternary amino groups. The nanoparticles described herein also can be functionalized with unsaturated groups such as vinyl and allyl groups.

The nanoparticles, as isolated and purified, can be either directly functionalized or indirectly, where one or more intermediate linkers or spacers can be used. The nanoparticles can be subjected to one or more than one functionalization steps including two or more, three or more, or four or more functionalization steps.

Functionalized nanoparticles can be further conjugated with various desired molecules, which are of interest for a variety of applications, such as biomolecules, small molecules, therapeutic agents, micro- and nanoparticles, pharmaceutically active moieties, macromolecules, diagnostic labels, chelating agents, dispersants, charge modifying agents, viscosity modifying agents, surfactants, coagulation agents and flocculants, as well as various combinations of these chemical compounds.

Known methods for polysaccharide functionalization or derivatization can be used. For example, one approach is the introduction of carbonyl groups, by selective oxidation of glucose hydroxyl groups at positions of C-2, C-3, C-4 and/or C-6. There is a wide spectrum of oxidative agents which can be used such as periodate (e.g., potassium periodate), bromine, dimethyl sulfoxide/acetic anhydride (DMSO/Ac$_2$O) [e.g., U.S. Pat. No. 4,683,298], Dess-Martin periodinane, etc.

The nanoparticles described herein when functionalized with carbonyl groups are readily reactive with compounds bearing primary or secondary amine groups. This results in imine formation which can be further reduced to amine with a reductive agent e.g., sodium borohydrate. Thus, the reduction step provides an amino-product that is more stable than the imine intermediate, and also converts unreacted carbonyls in hydroxyl groups. Elimination of carbonyls significantly reduces the possibility of non-specific interactions of derivatized nanoparticles with non-targeted molecules, e.g. plasma proteins. The reaction between carbonyl- and amino-compounds and the reduction step can be conducted simultaneously in one vessel (with a suitable reducing agent introduced to the same reaction mixture). This reaction is known as direct reductive amination. Here, any reducing agent, which selectively reduces imines in the presence of carbonyl groups, e.g., sodium cyanoborohydrate, can be used.

For the preparation of amino-functionalized nanoparticles from carbonyl-functionalized nanoparticles, any ammonium salt or primary or secondary amine-containing compound can be used, e.g., ammonium acetate, ammonium chloride, hydrazine, ethylenediamine, or hexanediamine. This reaction can be conducted in water or in an aqueous polar organic solvent e.g., ethyl alcohol, DMSO, or dimethylformamide.

Reductive amination of the nanoparticles described herein can be also achieved by using the following two step process. The first step is allylation, i.e., converting hydroxyls into allyl-groups by reaction with allyl halogen in the presence of a reducing agent, e.g., sodium borohydrate. In the second step, the allyl-groups are reacted with a bifunctional aminothiol compound, e.g., aminoethanethiol.

Amino-functionalized nanoparticles are amenable to further modification. For example, amino groups are reactive to carbonyl compounds (aldehydes and ketones), carboxylic acids and their derivatives, (e.g., acyl chlorides, esters), succinimidyl esters, isothiocyanates, sulfonyl chlorides, etc.

In certain embodiments, the nanoparticles described herein are functionalized using the process of cyanylation. This process results in the formation of cyanate esters and imidocarbonates on polysaccharide hydroxyls. These groups react readily with primary amines under very mild conditions, forming covalent linkages. Cyanylation agents such as cyanogen bromide, and, preferably, 1-cyano-4-diethylamino-pyridinium (CDAP), can be used for functionalization of the nanoparticles.

Functionalized nanoparticles can be directly attached to a chemical compound bearing a functional group that is capable of binding to carbonyl- or amino-groups. However, for some applications it may be important to attach chemical compounds via a spacer or linker including for example a polymer spacer or a linker. These can be homo- or hetero-bifunctional linkers bearing functional groups which include, but are not limited to, amino, carbonyl, sulfhydryl, succimidyl, maleimidyl, and isocyanate e.g., diaminohexane, ethylene glycobis(sulfosuccimidylsuccinate) (sulfo-EGS), disulfosuccimidyl tartarate (sulfo-DST), dithiobis (sulfosuccimidylpropionate) (DTSSP), aminoethanethiol, and the like.

Chemical Compounds and Modifiers for the Nanoparticles/Conjugation

In certain embodiments, chemical compounds which can be used to modify the nanoparticles described herein include, but are not limited to: biomolecules, small molecules, therapeutic agents, micro- and nanoparticles, pharmaceutically active moieties, macromolecules, diagnostic labels, chelating agents, dispersants, charge modifying agents, viscosity modifying agents, surfactants, coagulation agents and flocculants, as well as various combinations of these chemical compounds.

In certain embodiments, biomolecules used as chemical compounds to modify the nanoparticles described herein include, but are not limited to, enzymes, receptors, neurotransmitters, hormones, cytokines, cell response chemical compounds such as growth factors and chemotactic factors, antibodies, vaccines, haptens, toxins, interferons, ribozymes, anti-sense agents, and nucleic acids.

In certain embodiments, small molecule modifiers of the nanoparticles described herein can be those which can be useful as catalysts and include, but are not limited to, metal-organic complexes.

In certain embodiments, pharmaceutically useful moieties used as modifiers for the nanoparticles include, but are not limited to, hydrophobicity modifiers, pharmacokinetic modifiers, biologically active modifiers and detectable modifiers.

In certain embodiments, the nanoparticles can be modified with chemical compounds which have light absorbing, light emitting, fluorescent, luminescent, Raman scattering, fluorescence resonant energy transfer, and electroluminescence properties.

In certain embodiments, diagnostic labels of the nanoparticles include, but are not limited to, diagnostic radiopharmaceutical or radioactive isotopes for gamma scintigraphy and positron emission tomography (PET), contrast agents for Magnetic Resonance Imaging (MRI) (e.g. paramagnetic atoms and superparamagnetic nanocrystals), contrast agents for computed tomography, contrast agents for imaging with X-rays, contrast agents for ultrasound diagnostic methods, agents for neutron activation, and other moieties which can reflect, scatter or affect X-rays, ultrasounds, radiowaves and microwaves, fluorophores in various optical procedures, etc. Diagnostic radiopharmaceuticals include gamma-emitting radionuclides, e.g., indium-111, technetium-99m and iodine-131, etc. Contrast agents for MRI (Magnetic Resonance Imaging) include magnetic compounds, e.g. paramagnetic ions, iron, manganese, gadolinium, lanthanides, organic paramagnetic moieties and superparamagnetic, ferromagnetic and antiferromagnetic compounds, e.g., iron oxide colloids, ferrite colloids, etc. Contrast agents for computed tomography and other X-ray based imaging methods include compounds absorbing X-rays, e.g., iodine, barium, etc. Contrast agents for ultrasound based methods include compounds which can absorb, reflect and scatter ultrasound waves, e.g., emulsions, crystals, gas bubbles, etc. Other examples include substances useful for neutron activation, such as boron and gadolinium. Further, labels can be employed which can reflect, refract, scatter, or otherwise affect X-rays, ultrasound, radiowaves, microwaves and other rays useful in diagnostic procedures. In certain embodiments a modifier comprises a paramagnetic ion or group.

In certain embodiments, two or more different chemical compounds are used to produce multifunctional derivatives. For example, the first chemical compound is selected from a list of potential specific binding biomolecules, such as antibody and aptamers, and then the second chemical compound is selected from a list of potential diagnostic labels.

In certain embodiments, the nanoparticles described herein can be used as templates for the preparation of inorganic nanomaterials using methods that are generally known in the art (see, e.g. *Nanobiotechnology II*, Eds Mirkin and Niemeyer, Wiley-VCH, 2007.) This can include functionalization of the nanoparticles with charged functional groups, followed by mineralization which may include incubation of functionalized nanoparticles in solutions of various cations, e.g. metals, semiconductors. Mineralized nanoparticles described herein can be then purified and used in various applications, which include but are not limited to medical diagnostics, sensors, optics, electronics, etc.

Compositions

In one embodiment, the nanoparticle composition is in the form of an aqueous extract as obtained after the step of ultrafiltration.

In one embodiment, the nanoparticle composition is dried and the composition is a powder.

Dried nanoparticle compositions of the present invention are easily soluble/dispersible in water, glycerin and in some organic solvents such as dimethyl sulfoxide (DMSO) or dimethylformamide DMF. In one embodiment, the composition comprises the dried nanoparticles dispersed in water or a solvent. The monodisperse nanoparticle compositions have unique rheological properties compared to previous glycogen compositions. Aqueous dispersions of nanoparticle compositions of the present invention show no significant viscosity up to a concentration of 25% by weight. As a comparison, the "pure phytoglycogen" of Yao (WO 2013/019977) shows a viscosity at 15.2 w/w of 3.645 Pas (3645±315 mPas).

In one embodiment, the composition is shelf-stable at room temperature for at least 24 months from the date of manufacture.

Industrial Applicability

The compositions of monodisperse photoglycogen nanoparticles disclosed herein can be used in a wide range of food, personal care, industrial and medical applications. For example, the compositions can be used as an additive to control rheology, moisture retention and surface properties. Examples of applications include: film forming, low glycemic index source of carbohydrates, texture enhancers, dermal fillers, stabilizer for vitamins and other photosensitive bioactive compounds, pigment extender, medical lubricant and excipient, drug delivery agent. Compositions of the present invention can also be used to improve the UV protection of suncare formulations and to enhance the photostability of bioactives and other photolabile compounds, such as sunscreens, vitamins, and pharmaceuticals. Various applications are detailed in the international patent application entitled "Polyfunctional Glycogen and Phytoglycogen Additives", which is being filed concurrently herewith by the same applicant and the contents of which are incorporated by reference in their entirety.

The monodisperse phytoglycogen nanoparticles disclosed herein are particularly useful as film-forming agents. Because the nanoparticles are monodisperse, uniform close-packed films are possible. The compositions form stable films with low water activity. Water activity characterizes the degree to which a material can bind water and also the degree to which water molecules can migrate within the material. Water activity is important in the food industry, where it is necessary to find a balance between the physical strength of a product, which increases with its dryness, and the taste of a product, which often increases with higher moisture content. Control of water activity is particularly important in food products that contain several structurally different components, e.g. the bulk of a muffin and the icing coating on the top of the muffin. The composition of the present invention can be used as a barrier film between different components of food products. For example, if the food product is relatively dry, a concentrated aqueous solution of the monodisperse phytoglycogen nanoparticles of the present invention can be sprayed onto the surface of a food product component before another component is brought into contact with the first component and allowed to dry. For the case in which the food product already contains a substantial amount of moisture, a fine powder of the phytoglycogen nanoparticles can be sprinkled onto the surface of the first food component until a continuous film is formed, after which the second component is brought into contact. The composition forms a barrier film and substantially reduces diffusion of water molecules from one food component to another. This barrier film forming property can also be used in the manufacturing of drug and vitamin pills, for which diffusion of water between components is not desirable.

In one embodiment, the composition of monodisperse phytoglycogen nanoparticles disclosed herein are used for drug delivery. The monodisperse phytoglycogen nanoparticles are non-toxic, have no known allergenicity, and can be degraded by glycogenolytic enzymes (e.g. amylases and phosphorylases) of the human body. The products of enzymatic degradation are non-toxic, neutral molecules of glucose. The nanoparticles exhibit excellent chemical compound carrying capacity since they can be conjugated with drugs directly or via molecular spacers or tethers. The drug-conjugated nanoparticle can be further modified with specific tissue targeting molecules, such as folic acid, antibodies or aptamers. The low polydispersity allows uniform derivatization and drug distribution, and associated predictable pharmacokinetics. Finally, the compact spherical molecule, neutral charge and highly hydrophilicity are associated with efficient cell uptake.

EXAMPLE 1

Extraction of Glycogen (Phytoglycogen) from Sweet Corn Kernels 1 kg of frozen sweet corn kernels (75% moisture content) was mixed with 2 L of deionized water at 20° C. and was pulverized in a blender at 3000 rpm for 3 min. Mush was centrifuged at 12,000×g for 15 min at 4° C. The combined supernatant fraction was subjected to CFF using a membrane filter with 0.1 µm pore size. The filtrate was further purified by a batch diafiltration using membrane with MWCO of 500 kDa and at RT and diavolume of 6. (Diavolume is the ratio of total mQ water volume introduced to the operation during diafiltration to retentate volume.)

The retentate fraction was mixed with 2.5 volumes of 95% ethanol and centrifuged at 8,000×g for 10 min at 4° C. The retentate was mixed with 2.5 volumes of 95% ethanol and centrifuged at 8,000×g for 10 min at 4° C. The pellet containing phytoglycogen was dried in an oven at 50° C. for 24 h and then milled to 45 mesh. The weight of the dried phytoglycogen was 97 g.

According to DLS measurements, the phytoglycogen nanoparticles produced had particle size diameter of 83.0 nm and the polydispersity index of 0.081 (FIG. 2)

EXAMPLE 2

250 g of dry corn kernels of NK199 variety harvested at dent stage were ground to the particle size of less than 0.5 mm. Cold water extraction was performed at 20° C. with moderate agitation for 20 min. Insoluble components were precipitated by centrifugation at 8,000×g. Multistage microfiltration was performed on the supernatant with filtration media pore size of 10.0, 1.0 and 0.1 µm. Cross Flow Filtration (diafiltration) was performed with a MWCO of 300 kDa at RT and diavolume of 6. The retentate was mixed with 2.5 volumes of 95% ethanol and centrifuged at 8,000×g for 10 min at 4° C. The pellet containing phytoglycogen was dried in an oven at 50° C. for 24 h and then milled to 45 mesh. The weight of the dried glycogen was 17.5 g.

According to DLS measurements, the phytoglycogen nanoparticles produced had particle size diameter of 63.0 nm and a polydispersity index of 0.053 (FIG. 3)

EXAMPLE 3

Characterization of Corn Kernel Phytoglycogen of the Present Invention

Phytoglycogen nanoparticles prepared as in Example 2 of the present invention were characterized by DLS and the results are presented in Table 1. All cultivars are standard (su) type.

| Cultivar* | Yield, % on kernel abs dry wt | Particle size, nm | Polydispersity Index |
|---|---|---|---|
| Country Gentlemen | 24.78 | 68.8 | 0.103 |
| Sugar Dots | 28.02 | 69.4 | 0.081 |
| Jubilee | 27.25 | 66.9 | 0.086 |
| Stowell's Evergreen | 27.47 | 66.6 | 0.071 |
| NK199 | 28.46 | 63 | 0.053 |
| Honey and Cream | 32.64 | 68.8 | 0.103 |
| Silver Queen | 27.20 | 68.5 | 0.129 |
| Golden Bantam | 35.71 | 68.1 | 0.098 |
| Quickie | 31.43 | 63.9 | 0.118 |
| Earlivee Yellow | 31.81 | 77.5 | 0.107 |
| Early Sunglow | 23.79 | 69.6 | 0.099 |
| G90 | 29.01 | 67.1 | 0.087 |
| Seneca Horizon | 25.55 | 73.3 | 0.109 |
| Iochieff | 30.11 | 66.5 | 0.107 |
| Butter and Sugar | 30.05 | 75.3 | 0.075 |

The phytoglycogen nanoparticles produced had a polydispersity index between 0.071 and 0.129, with an average polydispersity index of 0.10.

EXAMPLE 3

Characterization of Corn Kernel Phytoglycogen of the Present Invention

Phytoglycogen nanoparticles prepared as in Example 2 of the present invention using corn kernels of se and sh type, harvested at the dent stage, were characterized and the results are presented in Table 2.

| Cultivar | Type | Yield, % on kernel dry wt | Particle size, nm |
| --- | --- | --- | --- |
| Navajo | se bicolor | 5.4 | 95.2 |
| Welcome | se yellow | 7 | 98.7 |
| Speedy Sweet | se bicolor | 7.2 | 60.3 |
| Fleet Bicolor | se bicolor | 9.5 | 95.1 |
| Head Start | se yellow | 17.3 | 88 |
| Aladdin | se bicolor | 20.4 | 92.1 |
| Sensor | se bicolor | 21.4 | 84.3 |
| Silver King | se white | 25.8 | 88.1 |
| Sensor | se bicolor | 21.1 | 102.8 |
| Delectable | se bicolor | 20.1 | 91.1 |
| Colorow | se yellow | 24 | 100.4 |
| Brocade | se bicolor | 20 | 115 |
| Trinity | se bicolor | 17.6 | 95.8 |
| Temptation | se bicolor | 14.2 | 94.2 |
| Sheba A | sh | 0 | — |
| Gourmet Obsession | sh | 0 | — |
| Gourmet 2281 | sh | 0 | — |
| Devotion | sh | 0 | — |

EXAMPLE 4

Figure 4:
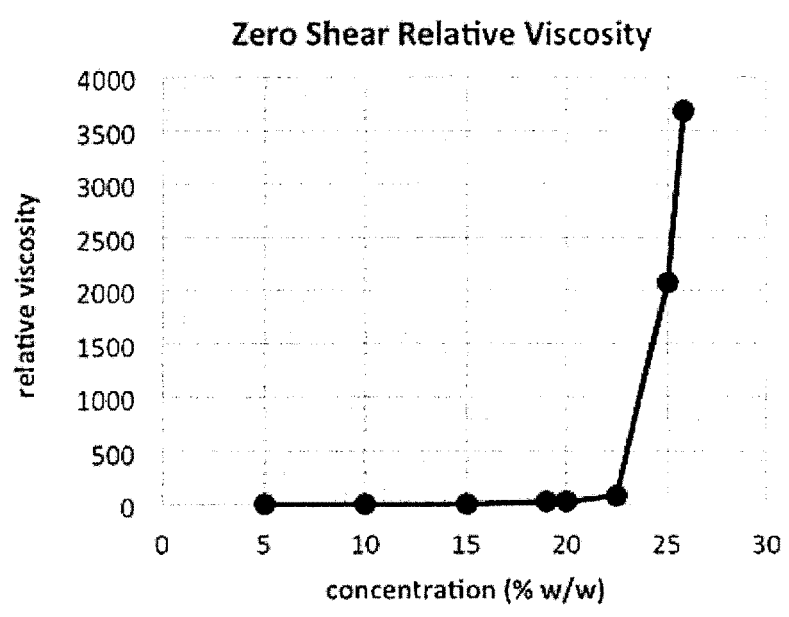
FIG. 4 shows viscosity versus concentration (w/w %) for a dispersion of monodisperse phytoglycogen nanoparticles in water according to an embodiment of the present invention.

Dried nanoparticle compositions of the present invention were dissolved in water at various concentrations from 5 to 30 w/w %. Results are shown in FIG. 4. Solutions provided were clear with no significant viscosity up to concentration of 25% by weight. Viscosity increased significantly for concentration greater than 25% w/w. For concentrations above 20% w/w the solutions showed strong shear thinning properties.

REFERENCES

1. Manners, *Carbohydrate Polymers,* 16 (1991) pp. 37-82.
2. Pflüger, 1894, *Archiv. für Physiologie,* pp 394-396.
3. Somogyi, 1934, *J. Biol. Chem.,* 104:245-253.
4. Stetten et al., 1956. *J. Biol. Chem.* 222, 587-599.
5. Bell and Young, 1934, *Biochem. J.* 28:882-890.
6. Orell et al., 1964, *J. Biol Chem.,* 239: 4021-4026.
7. Bueding and Orrell. *J. Biol Chem.* 1961, 236: 2854-7.
8. Huang and Yao, *Carbohydrate Polymers,* 2011, 83: 1165-1171.
9. Melendez-Hevia et al., (1993) Optimization of molecular design in the evolution of metabolism: the glycogen molecule, *Biochem. J.* 295: 477-483.
10. Meléndez et al., (1997) How did glycogen structure evolve to satisfy the requirement for rapid mobilization of glucose? A problem of physical constraints in structure building. *J. Mol. Evol.* 45:446-455.
11. Meléndez et al., (1998) Physical constraints in the synthesis of glycogen that influence its structural homogeneity: a two-dimensional approach. *Biophys. J.* 75: 106-114.
12. Meléndez et al., (1999) The fractal structure of glycogen: a clever solution to optimize the cell metabolism. *Biophys. J.* 77:1327-1332.
13. DiNuzzo M. (2013) Kinetic analysis of glycogen turnover: relevance to human brain (13) C-NMR spectroscopy. *Journal of cerebral blood flow and metabolism* 33:1540-1548.
14. Thompson, D. B. (2000) *Carbohydr. Res.* 43: 223-239.

What is claimed is:

1. A composition comprising phytoglycogen nanoparticles obtained from a phytoglycogen-containing plant material, wherein the phytoglycogen-containing plant material is obtained from standard type (su) or sugary extender (se) type sweet corn, the phytoglycogen nanoparticles having a polydispersity index of less than 0.3 as measured by dynamic light scattering (DLS).

2. The composition of claim 1, wherein the phytoglycogen nanoparticles have a polydispersity index of less than 0.2 as measured by DLS.

3. The composition of claim 2, wherein the phytoglycogen nanoparticles have a polydispersity index of less than 0.1 as measured by DLS.

4. The composition of claim 1, wherein the phytoglycogen nanoparticles have an average particle diameter of between about 30 nm and about 150 nm.

5. The composition of claim 4, wherein the phytoglycogen nanoparticles have an average particle diameter between about 60 nm and 110 nm.

6. The composition of claim 4, wherein the composition based on dry weight comprises more than 80% phytoglycogen nanoparticles having an average particle diameter of between about 30 nm and 150 nm.

7. The composition of claim 6, wherein the composition based on dry weight comprises more than 90% phytoglycogen nanoparticles having an average particle diameter of between about 30 nm and 150 nm.

8. The composition of claim 7, wherein the composition based on dry weight comprises more than 99% phytoglycogen nanoparticles having an average particle diameter of between about 30 nm and 150 nm.

9. The composition of claim 5, wherein the composition based on dry weight comprises more than 80% phytoglycogen nanoparticles having an average particle diameter of between about 60 nm and 110 nm.

10. The composition of claim 9, wherein the composition based on dry weight comprises more than 90% phytoglycogen nanoparticles having an average particle diameter of between about 60 nm and 110 nm.

11. The composition of claim 10, wherein the composition based on dry weight comprises more than 99% phytoglycogen nanoparticles having an average particle diameter of between about 60 nm and 110 nm.

12. The composition of claim 1, wherein the phytoglycogen-containing plant material is obtained from milk stage or dent stage corn kernels.

13. The composition of claim 1, wherein the composition is a powder.

14. The composition of claim 1, wherein the composition is an aqueous dispersion of the phytoglycogen nanoparticles.

15. The composition of claim 1, wherein the composition is a film-forming agent.

16. The composition of claim 1, wherein the composition is a drug-delivery agent.

17. A method of producing monodisperse phytoglycogen nanoparticles comprising:

a. immersing disintegrated a phytoglycogen-containing plant material in water at a temperature between about 0 and about 50° C.;
b. subjecting the product of step (a.) to a solid-liquid separation to obtain an aqueous extract;
c. passing the aqueous extract of step (b.) through a microfiltration material having a maximum average pore size of between about 0.05 and 0.15 μm; and
d. subjecting the filtrate from step c. to ultrafiltration to remove impurities having a molecular weight of less than 300 kDa to obtain an aqueous composition comprising monodisperse phytoglycogen nanoparticle, having a polydispersity index of less than 0.3 as measured by dynamic light scattering (DLS).

18. The method of claim 17, wherein the phytoglycogen-containing plant material is a cereal.

19. The method of claim 18, wherein the cereal is corn, rice, barley, sorghum or a mixture thereof.

20. The method of claim 19, wherein the phytoglycogen-containing plant material is standard type (su) or surgary extender (se) type sweet corn.

21. The method of claim 20, wherein the phytoglycogen-containing plant material is milk stage or dent stage kernel of standard type (su) or surgary extender (se) type sweet corn.

22. The method of claim 17 comprising step (e.) subject the aqueous composition comprising monodisperse phytoglycogen nanoparticles to enzymatic treatment using amylosucrose, glycosyltransferase, branching enzymes or any combination thereof.

23. The method of claim 17, further comprising adding an adsorptive filtration aid prior to step c or step d.

24. The method of claim 23 wherein the adsorptive filtration aid is a diatomaceous earth.

25. The method of claim 17, wherein the solid-liquid separation comprises agitating the product of step (a.) for a period of 10 to 30 minutes.

26. The method of claim 17 wherein the ultrafiltration of step (d.) removes impurities having a molecular weight less than about 500 kDa.

27. The method of claim 17, wherein step c. comprises passing the aqueous extract of step (b.) through (c.1) a first microfiltration material having a maximum average pore size between about 10 μm and about 40 μm; (c.2) a second microfiltration material having a maximum average pore size between about 0.5 μm and about 2.0 μm, and (c.3) a third microfiltration material having a maximum average pore size between about 0.05 and 0.15 μm.

28. The method of claim 17, further comprising centrifuging the product of step b.

29. The method of claim 17, further comprising (e.1) drying the aqueous composition comprising monodisperse phytoglycogen nanoparticles to yield a dried composition of monodisperse phytoglycogen nanoparticles.

30. A composition comprising monodisperse nanoparticles produced according to the method of claim 17.

* * * * *